United States Patent

Richtzenhain et al.

[11] 4,091,017
[45] May 23, 1978

[54] METHOD OF PREPARING TEREPHTHALIC ACID DICHLORIDE AND ISOPHTHALIC ACID DICHLORIDE

[75] Inventors: Hermann Richtzenhain, Much-Schellenbach; Paul Riegger, Troisdorf, Sieglar, both of Germany

[73] Assignee: Dynamit Nobel Aktiengesellschaft, Troisdorf Bez. Koeln, Germany

[21] Appl. No.: 704,279

[22] Filed: Jul. 12, 1976

Related U.S. Application Data

[63] Continuation of Ser. No. 513,782, Oct. 10, 1974, abandoned.

[30] Foreign Application Priority Data

Oct. 11, 1973 Germany .............................. 2351030

[51] Int. Cl.² .............................................. C07C 51/58
[52] U.S. Cl. ................................................. 260/544 D
[58] Field of Search ..................................... 260/544 D

[56] References Cited

U.S. PATENT DOCUMENTS

| | | | |
|---|---|---|---|
| 2,791,608 | 5/1957 | Golding | 260/544 D |
| 3,835,187 | 9/1974 | Tyson | 260/544 D |

FOREIGN PATENT DOCUMENTS

| | | | |
|---|---|---|---|
| 711,730 | 6/1965 | Canada | 260/544 D |
| 513,782 | 6/1941 | Germany | 260/544 D |

*Primary Examiner*—Norman Morgenstern
*Attorney, Agent, or Firm*—Burgess, Dinklage & Sprung

[57] ABSTRACT

Production of terephthalic acid dichloride and isophthalic acid dichloride by hydrolysis with water as a gas according to the following overall reaction:

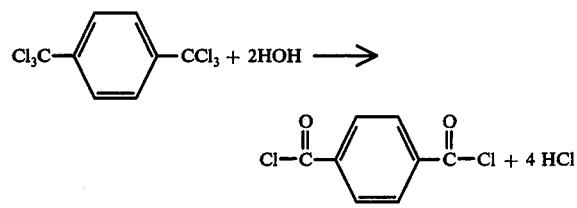

A Friedel-Crafts catalyst is used and some of the dichloride produced is maintained present throughout the reaction. The reaction is fast and the yield is high.

17 Claims, 1 Drawing Figure

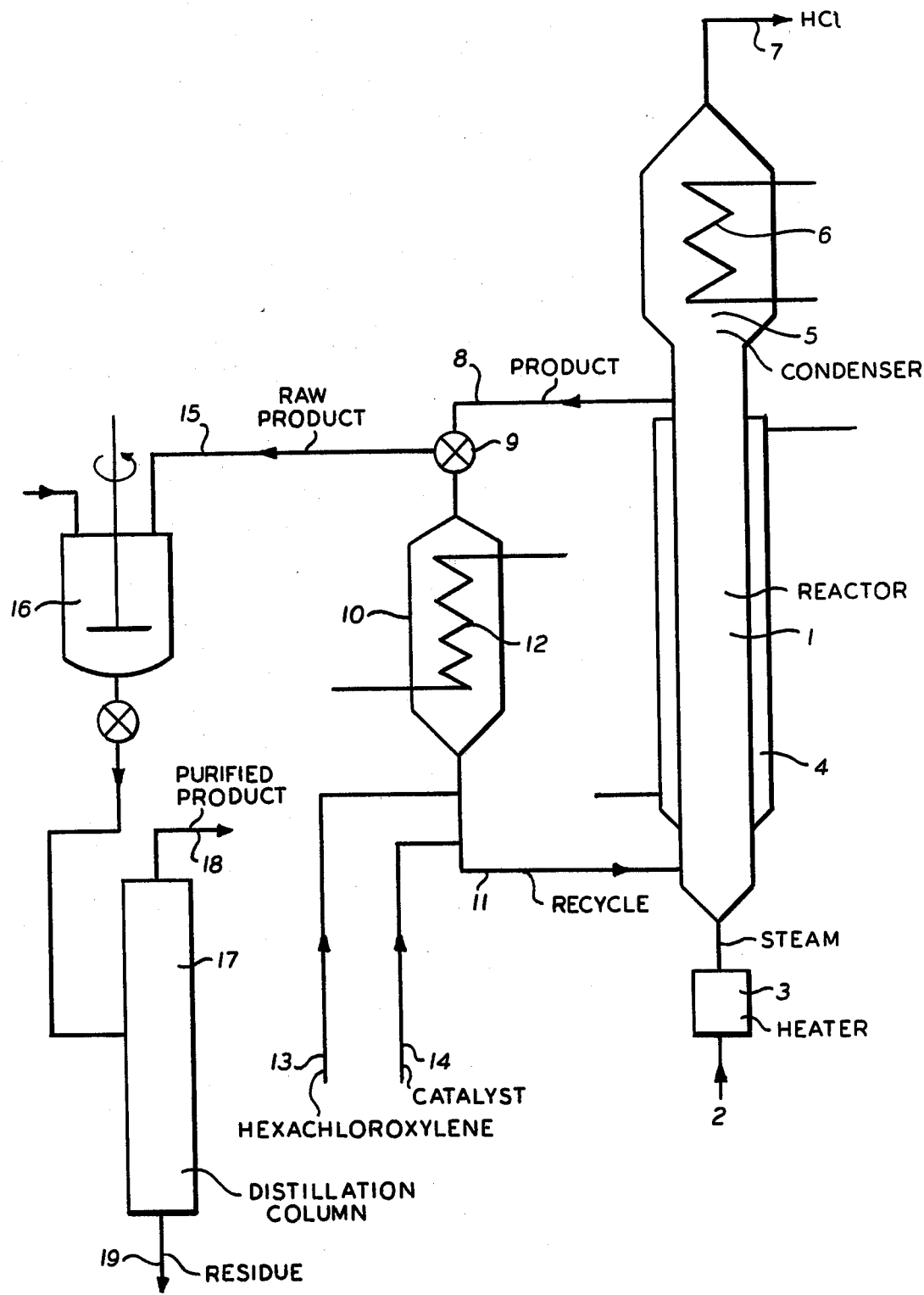

METHOD OF PREPARING TEREPHTHALIC ACID DICHLORIDE AND ISOPHTHALIC ACID DICHLORIDE

This is a continuation of application Ser. No. 513,782 filed Oct. 10, 1974 now abandoned.

BACKGROUND

The subject matter of the present invention is a method of preparing terephthalic acid dichloride and isophthalic acid dichloride by the partial hydrolysis of p-xylene and m-xylene, respectively, which are perchlorinated in the side chain, said partial hydrolysis being performed in the presence of Friedel-Crafts catalysts.

According to German Pat. No. 708,149 (IG-Farben 1936), terephthalic acid dichloride is formed by hydrolysis, by pouring water into 1,4-bis-(trichloromethyl)-benzene, heated at 125°–140° C, in the presence of iron (III) chloride or aluminum chloride.

Also known is the preparation of terephthalic or isophthalic acid dichloride by the reaction of 1,4- or 1,3-bis-(trichloromethyl)-benzene with the corresponding phthalic acids, with or without the aid of Friedel-Crafts catalysts, in accordance with German "Auslegeschrift" No. 1,196,636, among others, in which a mixture of the trichloride and terephthalic acid or isophthalic acid, heated to about 100° to 130° C, is introduced continuously into a reaction zone maintained at a temperature of approximately 270° to 330° C, or else the trichloride is poured into a melt of terephthalic or isophthalic acid dichloride, and the reaction mixture obtained in each case is processed.

The last-named method is disadvantageous, because one starts out with two starting substances, and, in the case of the continuous reaction, one must first separately combine the starting materials by melting them, adding the isophthalic acid or terephthalic acid in solid form, and then cooling and crushing them. Moreover, it is necessary without catalyst to operate at the very high temperatures of 270° to 330° C.

The first-named method of preparing isophthalic acid dichloride or terephthalic acid dichloride from only one starting substance, through the direct hydrolysis of the particular bis-(trichloromethyl)-benzene (hexachloroxylene), seems simple, but it entails the following difficulties:

The speed of the reaction of the hexachloroxylenes with water is substantially lower, under comparable conditions, than that of the reaction of the hexachloroxylenes with the phthalic acid in question. Consequently, in the case of a relatively large throughput, unreacted water escapes as water vapor with the hydrogen chloride and carries hexachloro-p-xylene and acid chloride with it. In the pipelines and stripping apparatus that follow, hydrolysis to phthalic acids takes place, resulting in deposits which are difficult to remove and in clogging. In addition, Friedel-Crafts catalysts, especially FeCl$_3$, when used in the direct hydrolysis of hexachloroxylenes with the yielding of HCl, bring about the formation of condensation products which, when the detention time is long and the temperatures are high, amount to considerable quantities and greatly diminish the yield in the distillation. But of all the Friedel-Crafts catalysts it is precisely FeCl$_3$ that has the greatest accelerating effect at relatively low temperatures.

THE INVENTION

The subject matter of the invention is a method for the preparation of terephthalic acid dichloride and isophthalic acid dichloride by the partial hydrolysis of 1,4- and 1,3-bis-(trichloromethyl)-benzene, respectively, with water in the presence of Friedel-Crafts catalysts, followed by separation of the product by distillation, which is characterized in that the hydrolysis is performed in terephthalic acid dichloride and isophthalic acid dichloride, respectively, and with water as gas.

The hydrolysis of hexachloroxylenes in the corresponding acid chloride as solvent avoids the disadvantages cited above. At the same time the reaction is rapid, so that it can take place in the flow pipe, which makes it possible to perform the process continuously in a very attractive manner.

The speed of the reaction of the hexachloroxylenes, or the formation of HCl, as the case may be, is very great, amounting to a few seconds, so that the throughput of the reaction is limited by virtually nothing but the velocity of the ascending gases, the distribution of the gases, and, in some cases, on the rate of circulation in the circuit.

Surprisingly, in the presence of the acid chlorides, FeCl$_3$ causes no side reactions which form condensation products, and therefore it is preferred, although other Friedel-Crafts catalysts, such as aluminum chloride, for example are also usable.

The high speed of the hydrolysis performed in the method of the invention in the presence of acid chlorides as solvents is based on the supposed indirect course of the reaction: (a) Hydrolysis of the acid chloride to carboxylic acid (rapid); (b-1) Reaction of the carboxylic acid with the trichloromethyl group of the hexachloroxylene (rapid), and (b-2) Reaction of carboxylic acid with acid chloride to form anhydride (rapid) (hydrogen chloride being formed in each of these reactions), and (c) Reaction of the anhydride with trichloromethyl groups to form acid chloride (slower).

The above-mentioned steps determining the speed of the reaction correspond to the following equations, other partial reactions being also possible to a secondary extent:

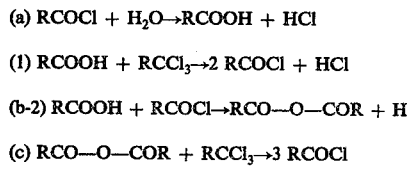

(a) RCOCl + H$_2$O → RCOOH + HCl (1) RCOOH + RCCl$_3$ → 2 RCOCl + HCl (b-2) RCOOH + RCOCl → RCO—O—COR + HCl (c) RCO—O—COR + RCCl$_3$ → 3 RCOCl (R here represents the particular aryl radical, which is further substituted in an appropriate manner.)

The process is very preferably performed in a continuous manner, but may also be performed discontinuously.

The continuous process can advantageously be performed in a circulatory apparatus in which vertically rising gases produce the circulation, much the same as in a circulatory evaporator.

The reactor can be a vertically disposed tube, preferably a temperature-controlled jacketed tube, into the bottom of which water is introduced, preferably as water vapor in finely divided form, through a nozzle, perforated plate, sintered diffuse, or other gas dispersing means. In addition, a pump can be provided in the circuit.

Along the reaction section, hydrogen chloride is formed, mainly by reactions a and b, and it is carried out through the opening at the top through a stripping condenser. The reactor operates as a bubble column, and in conjunction with a vertical tube connected to it, which is temperature controlled through a heating coil, for example, it produces a circulation. In the circuit, the product discharge, in the form of an overflow for example, the liquid hexachloroxylene feed, and the catalyst feed are arranged successively in descending order.

The discontinuous process can take place in a tank, preferably one provided with a stirrer, the tank being filled with acid chloride to such a depth that all of the water vapor is able to react. The water vapor is fed in at the bottom of the tank, and the hexachloroxylenes and catalyst are best also fed in close to the bottom, all at once or in partial quantities. The product can be taken from the tank, some of it being left for the next charge.

Both in the continuous and in the discontinuous embodiment, a superimposed stripper prevents the emergence of product and reactants with the hydrogen chloride.

The temperature control can be conducted by heating or, if necessary, by cooling. The catalyst, especially iron (III) chloride, is very preferably fed in the form of a solution in the acid chloride involved. The water vapor can be fed at temperatures between about 105° and 180° C, but preferably at the temperature prevailing in the reactor. The amount of water vapor is to be as close as possible to the stoichiometric amount of two moles of $H_2O$ per mole of bis-(trichloromethyl)-xylene. Any deviations from stoichiometry are detected by analysis of the product and corrected in the reactor or in an after-reaction vessel, in the manner described below.

The starting substances, 1,4- and 1,3-bis-(trichloromethyl)-benzene, can also be used in the form of a mixture. It is desirable that 0.5 to 20 times, and especially 1.2 to 5 times the volume of the terephthalic or isophthalic acid dichloride removed as raw product (line 15 of the accompanying drawing) be circulated in the apparatus as solvent.

The reaction temperature is to be in a range providing sufficiently great speed of reaction; therefore, it is to be between 110° and 180° C, in some cases as high as 250° C, and preferably between 120° and 160° C, especially between 130° and 150° C.

The catalyst concentration is between 0.01 and 1 wt.-%, preferably between 0.025 and 0.5 wt.-% $FeCl_3$, or an other Friedel-Crafts catalyst with respect to the hexachloroxylenes put in.

The raw product is withdrawn very preferably continuously, preferably into a stirring vessel connected to the product discharge of the reactor. The composition of the product depends on the stoichiometric proportioning of water and the bis-(trichloromethyl)-xylene.

An excess of water results in anhydridic condensation products (I) which undesirably appear as a residue in the distillation, and an excess of trichloromethyl compound results in trichloromethylbenzoylchloride (II). The content of (I) can be determined in the stirring vessel, serving as an intermediate tank by distilling a specimen and the content of (II) can be determined by the gas-chromatographic analysis of the distillate. Correction can be made by the addition of terephthalic or isophthalic acid in the case of the occurrence of (II), or by addition of the particular bis-(trichloromethyl)-benzene in the case of the occurrence of (I).

After degassing has been completed, the contents are transferred to a supply tank serving as the starting point for the separation of the product, from which, preferably, a continuously operating distillation system is fed.

The acid chlorides produced are obtained in pure form, virtually free of by-products. The yields are then very high, ranging from 99.5 to 100% of the theory.

When hexachloroxylenes are used which contain residues of by-products formed in their preparation in amounts, for example, of 0.5 to 4% by weight, or, in borderline cases, up to about 8% by weight, these by-products do not interfere with the reaction nor do they diminish the high rate of transformation of the hexachloroxylenes. The low-volatility by-products remain in the residue after the distillation and can thus be easily removed together with the catalyst and in some cases can be utilized.

The dichlorides of terephthalic or isophthalic acid thus prepared can be used in a known manner, for example, for the preparation of polyesters.

Thus, the invention provides a process for producing at least one of terephthalic acid dichloride and isophthalic acid dichloride by hydrolysis of the corresponding bis-trichloromethyl benzene with water in the presence of a Friedel-Crafts catalyst. According to the invention, the hydrolysis is carried out while maintaining at least one of said dichlorides present throughout the hydrolysis. That is to say that at least one of the dichlorides is present initially during the hydrolysis.

EXAMPLE 1

In a circulatory apparatus as described above, 17 kg of hexachloro-p-xylene (98% purity) at 130° C, 1.94 kg of water in the form of superheated steam at 125° to 135° C, and 0.1 kg of 5 wt.-% solution of $FeCl_3$ in terephthalic acid dichloride at 130° C were fed uniformly each hour. The reaction vessel consists of a jacketed tube of an inside diamter of 100 mm and a liquid level of 1,300 mm. The reaction temperature is 138° to 142° C.

The stripping condenser was supplied with water of 85° C on account of the solidification point of the dichloroide of 80° C. The escaping hydrogen chloride was freed of solids in a perchlorethylene washing tower. 11.k kg of raw terephthalic acid dichloride was removed per hour at the overflow outlet. The reaction was continued for 2.5 days without disturbance. After correction, degassing and distillation, 10.5 kg of colorless terephthalic acid dichloride were obtained per hour. Melting point 82° C. No residues of condensation products formed in the reaction were observed in the distillation. The yield is 99.9% with respect to the hexachloro-p-xylene content in the starting substance.

EXAMPLE 2

By repeating Example 1 in the described apparatus, but feeding 0.08 kg per hour of a 5 wt.-% solution of the catalyst at (a) 130° C and (b) 152° C, equally good results were obtained.

EXAMPLE 3

The following experiments show the effect of $FeCl_3$ on hexachloro-p-xylene, and especially on hexachloro-m-xylene, in the absence of previously formed acid chlorides.

One mole of hexachloroxylene is heated in a corresponding experimental apparatus in the presence of 0.1 wt.-% of $FeCl_3$ for 2 hours at 140° C, and the escaping amount of HCl is measured. Then the distillation residue was determined by gentle vacuum distillation.

|  | Moles of HCl | Residue |
|---|---|---|
| p-hexachloroxylene | 0.0128 | 2.6 wt. % |
| m-hexachloroxylene | 0.117 | 12.3 wt % |

The residue consists of condensation products in which two or more aryl nuclei are joined by side chains.

EXAMPLE 4

In the same manner and apparatus as in Example 1, 17 kg of hexachloro-m-xylene (purity 95% by weight) preheated to 130° C, 1.90 kg of water as superheated steam of 140° C, and 0.1 kg of 5% sultion of $FeCl_3$ in isophthalic acid dichloride are proportioned per hour at a uniform rate. At the overflow outlet, 11 kg/h of raw isophthalic acid dichloride is taken and, after correction, separated from the catalyst by distillation.

The yield amounted to 100% pure isophthalic acid dichloride, melting point 140° C, with respect to the content of hexachloro-m-xylene in the starting substance.

No residue of condensation products was found in the distillation.

The invention is further explained in the drawing with reference to an embodiment thereof.

FIG. 1 is a diagrammatic cross-sectional representation of a circulatory apparatus preferentially used for the performance of the process.

In the circulatory apparatus represented in FIG. 1, water, in the form of steam produced in the boiler and superheater 3, is fed through line 2 into the bottom of the vertical reactor tube 1. The reactor tube is equipped with a heating and cooling jacket 4 for controlling the temperature of the reaction mixture. The gases rising in the reactor—in the upper part only the hydrogen chloride that is formed—leave through the top of the reactor and pass through the superimposed stripping condenser 5 whose controlled-temperature cooling system 6 is kept at such a temperature that entrained, non-gaseous substances are not cooled below their solidification point and flow back into the reactor in liquid form. The hydrogen chloride is discharged from the top of the stripping condenser through line 7 and passes if desired, through a scrubber, which is not shown, for removal of any remainder of entrained substances.

The product is discharged through line 8 from the upper part of the reactor. Some of the product is fed back into the bottom of the reactor through the vertical tube 10 and line 11 in the circuit 8, 10 and 11.

The vertical tube 10 is temperature-controlled by means of the heating coil 12. Into line 11 are fed the hexachloroxylene starting material from line 13 and the catalyst solution from line 14, through a preheater, if descired, which is not shown. The portion of the product that is to be refined i.e. the "raw product" is removed from the circuit through an overflow or through a valve 9 if one is present, and line 15, and is fed through the intermediate tank 16, which can be provided with a stirrer, bottom valve and line for feeding a purification system comprising distillation column 17, for production of purified product 18 and residue 19.

The proportion of dichloride maintained present throughout the hydrolysis in relation to the amount of bis-trichloromethyl benzene present initially can be 0.4 - 22, preferably 1.1 - 6, parts of said dichloride to 1 part of bis-trichloromethyl benzene on a weight basis.

The relation of added bis-trichlormethyl benzene per hour to the inhoud of the apparatus generally may be 0.8 to 20, and especially 1.5 to 5 times of that inhoud.

In the examples 1, 2 and 4 at the beginning the reaktor of 100 mm inside diameter and a liquid level of 1,300 mm is filed with 7 kg of the respective dichloride containing 0.05 wt % $FeCl_3$ and is heated to 130° C.

Then the feed of the respective hexachloroxylene water and catelyst begins, the amounts of these materials fed in every hour beeing noted in the examples. Immediately the reaktion begins and HCl is developed, which amount of HCl gas causes the circulation in the apparatus.

The further dates given in the examples are measured in the state of balance of removed and recycled amounts.

What is claimed is:

1. In a process for producing at least one of terephthalic acid dichloride and isopthalic acid dichloride by hydrolysis of the corresponding bis-trichloromethyl benzene with water in the presence of a Friedel-Crafts catalyst, the improvement which comprises the water being a gas, and introducing said bis-trichloromethyl benzene, water, catalyst and said dichloride into a reaction zone for said hydrolysis, and maintaining at least one of said dichlorides present throughout the hydrolysis in the proportion of at least 0.4 parts of said dichloride to 1 part of the bis-trichloromethyl benzene present initially on a weight basis.

2. Process according to claim 1, wherein said bis-trichloromethyl benzene, water, catalyst nd said dichloride are introduced into a reaction zone for said hydrolysis, and the catalyst is introduced as a solution in said dichloride.

3. Process according to claim 1, wherein the catalyst is iron (III) chloride.

4. Process according to claim 1, wherein the hydrolysis is performed at 110°–180° C.

5. Process according to claim 1, wherein the hydrolysis is performed at 130°–150° C.

6. Process according to claim 1, wherein the acid dichloride is terephthalic acid dichloride.

7. Process according to claim 1, wherein the acid dichloride is isophthalic acid dichloride.

8. Process according to claim 1, wherein the bis-trichloromethyl benzene and water are used in a stoichiometric amount.

9. Process according to claim 1, said proportion being at least 1.1.

10. Process according to claim 1, wherein the process is performed continuously.

11. Process according to claim 10, wherein the reaction is performed in a vertically disposed reactor, by introduction of the bis-trichloromethyl benzene, water and catalyst into the reactor, maintaining the temperature at 110–180° C, hydrogen chloride being formed during the reaction and being withdrawn from the top of the reactor, the dichloride product being withdrawn from the reactor, and feeding some of the withdrawn dichloride product back into the reactor.

12. Process according to claim 11, wherein the water is introduced into the reactor as steam.

13. Process according to claim 12, wherein the bis-trichloromethyl benzene and water are used in a stoichiometric amount.

14. Process according to claim 11, wherein the bis-trichloromethyl benzene and water are used in a stoichiometric amount.

15. Process according to claim 10, wherein the bis-trichloromethyl benzene and water are used in a stoichiometric amount.

16. Process according to claim 1, wherein water is introduced into the reaction zone as steam.

17. Process according to claim 16, wherein the bis-trichloromethyl benzene and water are used in a stoichiometric amount.

* * * * *

UNITED STATES PATENT AND TRADEMARK OFFICE
CERTIFICATE OF CORRECTION

PATENT NO. : 4,091,017
DATED : May 23, 1978
INVENTOR(S) : Hermann Richtzenhain and Paul Riegger It is certified that error appears in the above-identified patent and that said Letters Patent are hereby corrected as shown below:

Title page, References cited, change "Tyson" to --Dyson--.

Column 6, line 34, change "nd" to --and--.

Signed and Sealed this

Thirty-first Day of October 1978

[SEAL]

Attest:

RUTH C. MASON
Attesting Officer

DONALD W. BANNER
Commissioner of Patents and Trademarks